United States Patent [19]

Mueller et al.

[11] Patent Number: 4,906,760

[45] Date of Patent: Mar. 6, 1990

[54] PURIFICATION OF ANHYDRIDES

[75] Inventors: Werner H. Mueller, Corpus Christi, Tex.; Suzanne Fontaine, Warwick, R.I.

[73] Assignee: Hoechst Celanese Corp., Somerville, N.J.

[21] Appl. No.: 228,631

[22] Filed: Aug. 4, 1988

[51] Int. Cl.$^4$ ............................................. C07D 307/89
[52] U.S. Cl. .................................... 549/239; 549/233; 549/241; 549/242; 549/250; 549/251
[58] Field of Search ............... 549/233, 239, 241, 242, 549/250, 251

[56] References Cited

U.S. PATENT DOCUMENTS 3,965,125  6/1976  Meyers et al. ...................... 549/241

Primary Examiner—Richard L. Raymond
Attorney, Agent, or Firm—Perman & Green

[57] ABSTRACT

Process for the purification of organic polyanhydrides to substantially-completely remove trace metals, such as for the production of metal-free electronic grade polymers. The process comprises decyclizing in an aqueous vehicle to form the polyacid, treating with an adsorption agent, crystallizing the polyacid, filtering and reconverting to the polyanhydride which is substantially free of trace metals. The purified polyanhydride can be reacted with other metal-free monomers to form metal-free polymers having excellent insulating properties for use in electrical components.

17 Claims, No Drawings

PURIFICATION OF ANHYDRIDES

BACKGROUND OF THE INVENTION

The present invention relates to a method for purifying anhydrides, particularly aromatic polyanhydrides such as bis phenyl furanediones, to form novel metal-free polyanhydrides suitable for reaction with other metal-free monomers to form metal-free polymers having excellent electro-resistive properties.

Aromatic polyanhydrides generally are produced by the liquid phase air oxidation or nitric acid oxidation of the corresponding alkyl aromatics in the presence of a metal salt catalyst. Such commercially-available polyanhydrides commonly contain from 100 to 500 parts per million of such metal salts in the form of impurities. For example crude commercially-available 2,2-bis-(3,4-dicarboxy phenyl) hexafluoropropane dianhydride (sometimes referred to as 5,5-[2,2,2-trifluoro-1-(trifluoromethyl) ethylidene]bis 1,3-isobenzofuranedione) (6F-DA) generally contains about 80 ppm sodium, 20 ppm iron, 30 ppm cobalt and 30 ppm manganese, for a total of about 160 ppm of these impurities. Prior known methods for the purification of crude commercially-available anhydrides result in partially purified anhydrides which still have an unduly high content of residual trace metals i.e., up to about 50 ppm of sodium, 10 ppm iron, 10 ppm cobalt and 10 ppm manganese, unless the purification procedure is repeated one or more times in order to remove the impurities in increments. Such incompletely purified polyanhydrides are not suitable for the formation of electronic grade polymers because the presence of such high amounts of trace metals in the formed polymers renders the polymers sufficiently electro-conductive that they are unsuitable for use in electronic components requiring electro-resistive properties. For example, polyimides used for electronic applications are required to be essentially free of metal ions and therefore must be produced by the reaction of substantially metal-free monomers or reactants, such as dianhydrides and diamines. A preferred class of polyimides comprises the high temperature-resistant fluorinated polyimides formed by the reaction of fluorinated aromatic polyanhydrides such as 6F-DA or 12F-DA with fluorinated or unfluorinated polyamines, such as 2,2-bis (3 aminophenyl) hexafluoropropane or 4,4'diamino-phenyl ether.

One method for purifying and clarifying aromatic polyanhydrides comprises dissolving the polyanhydride in acetone, adding absorbent such as carbon to clarify the solution, filtering, distilling off the acetone, adding toluene to crystallize out the purified polyacid, and adding acetic anhydride to convert any formed polyacid back to the cyclic polyanhydride. Generally the polyanhydride is initially formed in the presence of a metal salt catalyst by cyclization of a polyacid and this anhydride contains substantial trace amounts of metal from the catalyst and/or from other sources which cannot be completely removed in a single operation by washing, carbon desorption or other conventional purification systems. Repeated purification procedures do remove substantial additional amounts of the trace impurities, to about the same extent as the present purification process, but the repetition of the purification steps is time-consuming and otherwise disadvantageous.

Reference is made to U.S. Pat. Nos. 2,985,665; 2,518,312; 3,529,017; 3,544,602 and 3,965,125 for their disclosures of prior known processes for producing and/or purifying organic anhydrides.

Reference is also made to U.S. Pat. Nos. 4,592,925 and 3,959,350 for their disclosure of processes for the formation of polyimides from aromatic polyanhydrides and polyamines.

SUMMARY OF THE INVENTION

The present invention is based upon the discovery that crude and/or technical grade organic anhydrides can be purified of substantial trace amounts of metal ion impurities in a single purification procedure by refluxing the anhydride in an aqueous solution to decyclize the anhydride and to ionize or dissolve the metal impurities in the water vehicle, providing an activated adsorption agent such as activated carbon to clarify the solution, filtering off the adsorption agent (and recovering polyacid therefrom by washing the filter cake with warm water for return to the main solution) allowing the solution to stand and cool and precipitate the purified polyacid, filtering and washing the polyacid and finally recyclizing the polyacid back to the purified anhydride.

It appears that the decyclizing or opening of the anhydride ring, while the anhydride compound is dissolved in water, causes the metal impurities to ionize in the water vehicle, so that they can be removed from the precipitated acid by filtration. The carbon filter cake preferably is washed with water at about 90° C. to recover any of the polyacid therefrom, which is returned to the hot aqueous solution to preserve a high overall yield, greater than about 90%. This is important in cases where the anhydride is expensive, such as 6F-DA and 12F-DA (4,4'-bis[2(3,4-dicarboxyphenyl) hexafluoropropyl]diphenyl ether dianhydride). The purified polyacid is then recrystallized from the hot aqueous solution by the simple step of cooling the aqueous solution, and the crystalline purified polyacid is reconverted to the anhydride, such as by heating at elevated temperatures for several hours, to produce a high overall yield of the purified anhydride containing less than about 10 ppm each of sodium and iron, and less than about 5 ppm each of cobalt and manganese. A crude anhydride starting material contains about 80 ppm sodium, 20 ppm iron, 30 ppm cobalt and 30 ppm manganese, and a technical grade anhydride starting material contains about 25 ppm sodium, 20 ppm iron, 5 ppm cobalt and 5 ppm manganese.

The following examples are illustrative of processes which are within the scope of the present invention.

EXAMPLE 1

550 g of 6F-DA "crude" (available from Hoechst Celanese), 2750 g of distilled $H_2O$ and 80 g of Darco (activated charcoal) were charged to a 5000 ml flask and heated to reflux for 1.5 hrs., whereupon all the 6F-DA went into solution. The carbon was removed by pressure filtration at 85° C., and the filter cake was washed with 250 g of 90° C. water which was returned to the flask. Upon standing overnight, 6F-Tetraacid precipitated. It was filtered off and washed with 150 mls of distilled water. The yield was 784.4 g of moist cake. Yield of the dried cake (60° C./12 hrs.) was 537.3 g =90.3%. Heating a first portion of the cake to 160° C. for 4 hrs. and a second portion of the cake to 190° C. for 4 hrs. converts the 6F-Tetraacid (6F-TA) back to 6F-Dianhydride (6F-DA).

The purification effects of this procedure can be seen in Table 1, which follows. Table 1 shows the melting points, dianhydride and tetraacid contents and metal contents of the crude 6F-DA starting material, the 6F-TA produced according to Example 1, prior to reformation of the purified 6F-DA, the purified 6F-DA formed by converting the purified 6F-TA back to the 6F-DA according to Example 1.

reconversion to the purified polyanhydrides. The use of an aqueous vehicle is advantageous over prior used volatile organic vehicles, and the ability to separate out the purified crystalline polyacid by mere cooling of the aqueous vehicle is also an important advantage.

It will be appreciated that the present invention is applicable to the purification of organic polyanhydrides in general, most preferably aromatic dianhydrides,

TABLE 1

| | Melting Point | | Drying Conditions | Assay | | | Metals (PPM) | | | | | |
|---|---|---|---|---|---|---|---|---|---|---|---|---|
| | Onset | Max | °C./Hrs. | 6F-DA | 6F-MA | 6F-TA | $H_2O$ | Na | K | Fe | Co | Mn |
| 6F-DA-Crude | 241.7 | 243.6 | 160/4 | 91.8 | 1.9 | 1.2 | | 82 | 5 | 23 | 33 | 28 |
| 6F-Tetraacid (6F-TA) | | | 48/12 | — | — | 98.3 | 1.7 | 3 | <1 | 4 | <1 | <1 |
| 6F-DA (Purified) | 244.9 | 247.5 | 160/4 | 92.9 | 4.8 | 0.8 | — | 3 | <1 | 4 | <1 | <1 |
| 6F-DA (Purified) | 245.9 | 247.5 | 190/4 | 98.0 | 0.5 | — | — | na* | na | na | na | na |

*not analyzed

EXAMPLE 2

550 g 6F-DA "technical grade" (available from Hoechst Celanese Corporation) were treated as in Example 1. After filtration 764.4 g of the moist cake (68.5% solids) were transferred to a 5 L flask, equipped with stirrer, Dean Stark trap, thermometer and reflux condenser. 1600 ml of toluene were added and heating was started. At about 80° C. the 6F-TA dissolved in the aqueous phase. After about 3 hours at reflux, about 250 ml of water had separated. After water separation ceased, 455 g of acetic acid anhydride were added and reflux continued for 2 hrs., after which the mixture was allowed to cool to 27° C. After filtration, the filter cake was washed with 150 mls of heptane and dried at 60° C. in vacuum, to give white needles.

Overal yield: 80%

The purification effect can be seen in Table 2 which provides information similar to that given in Table 1.

which are insoluble in water at or below room temperature and are soluble in water at elevated temperatures, such as above about 50° C. Other suitable polyanhydrides include oxydiphthalic dianhydride,, benzophenone tetracarboxylic dianhydride and 3,3', 4,4'- diphenyl tetracarboxylic acid dianhydride, among others.

It should be understood that the foregoing description is only illustrative of the invention. Various alternatives and modifications can be devised by those skilled in the art without departing from the invention. Accordingly, the present invention is intended to embrace all such alternatives, modifications and variances which fall within the scope of the appended claims.

We claim:

1. Process for the purification of commercially-available aromatic anhydrides to substantially reduce the content of metal salt impurities therein, comprising the steps of:

(1) dissolving a commercially-available aromatic an-

TABLE 2

| | Melting Point | | Drying Conditions | Assay | | | Metals (PPM) | | | |
|---|---|---|---|---|---|---|---|---|---|---|
| | Onset | Max. | °C./Hrs. | 6F-DA | 6F-MA | 6F-TA | Na | Fe | Co | Mn |
| 6F-DA-Technical | 243.5 | 245 | 160/4 | 92.7 | 3.0 | 2.1 | 24 | 20 | 6 | 5 |
| 6F-Tetraacid (6F-TA) | | | 60/4 | — | 0 | 100 | 1.8 | 7.7 | <1 | <1 |
| 6F-DA-Purified | 246.4 | 247.7 | 60/4 | 99.5 | 0.5 | — | 1.1 | 0.3 | <1 | <1 |

EXAMPLE 3

100 g of commercially available PMDA (pyromellitic dianhydride) (Na 5.6 ppm and Fe 17 ppm) was charged to a 1 L flask and refluxed with 400 ml of distilled water. After about 1 hr. all was in solution. 5 g of Norite were added, the mixture clarified and the solution was allowed to cool to room temperature. The white precipitate was filtered off, dried at 60° C. in a vacuum.

The resulting purified tetraacid (PMTA) was converted back to the purified PMDA by refluxing with 240 ml of toluene and 190 ml of acetic anhydride. After filtration and drying in a vacuum oven at 40° C. 90.1 g, purified PMDA was recovered containing only about 3.1 ppm sodium and about 6.5 ppm iron.

It can be seen from the foregoing Examples and Tables that the present invention provides a relatively simple method for purifying crude or technical grade organic polyanhydrides in an aqueous medium, and for the recovery of the purified intermediate polyacids for hydride in an aqueous vehicle at elevated temperatures to convert the anhydride to the corresponding polyacid and to ionize the metal salt impurities in the aqueous vehicle, (2) exposing the aqueous solution of the polyacid to an adsorption agent, (3) separating out the adsorption agent, (4) reducing the temperature of the aqueous solution of the polyacid to cause the polyacid to crystallize out of solution in purified form, (5) filtering the moist purified crystalline polyacid, and (6) cyclizing the crystalline polyacid to form the original aromatic anhydride in purified form.

2. Process according to claim 1 in which the commercially-available aromatic anhydride is an aromatic dianhydride.

3. Process according to claim 2 in which the aromatic dianhydride is polyfluorinated.

4. Process according to claim 3 in which the polyfluorinated dianhydride is 2 2, bis (3,4-dicarboxyl phenyl)-hexafluoropropane dianhydride.

5. Process according to claim 1 in which step (1) is conducted under reflux temperatures.

6. Process according to claim 1 in which the adsorption agent comprises activated charcoal.

7. Process according to claim 1 in which step (4) is conducted by permitting the aqueous solution to cool to room temperature.

8. Process according to claim 1 in which the cyclizing step (6) includes the step of heating the polyacid to a temperature above about 160° C. for a time sufficient to cyclize substantially all of the polyacid present.

9. Process according to claim 1 in which the cyclizing step (6) is conducted by the steps of:
 (a) adding a water-immiscible organic vehicle to the moist purified crystalline polyacid of step (5) of claim 1,
 (b) heating the mixture to cause the polyacid to dissolve in the aqueous phase and refluxing to separate the water phase from the organic vehicle phase,
 (c) adding acetic acid anhydride and refluxing to form the original aromatic anhydride and to cause the purified aromatic anhydride to crystallize out of the aromatic vehicle in purified form, and
 (d) filtering the purified crystalline anhydride from the aromatic vehicle.

10. Process according to claim 9 in which the purified crystalline aromatic anhydride is washed with an organic non-solvent and dried to form the dry crystalline purified aromatic anhydride.

11. Process according to claim 9 in which the aromatic anhydride is an aromatic dianhydride.

12. Process according to claim 11 in which the aromatic dianhydride is polyfluorinated.

13. Process according to claim 12 in which the polyfluorinated dianhydride is 2,2 bis (3,4-dicarboxyl phenyl)- hexafluoropropane dianhydride.

14. Process according to claim in which the cyclizing step (6) is conducted by the steps of:
 (a) adding a water-immiscible organic vehicle and acetic anhydride to the purified crystalline polyacid of step (5) of claim 1 after drying thereof,
 (b) refluxing to convert the polyacid to the corresponding anhydride, and
 (c) separating the purified anhydride from the organic vehicle.

15. Process according to claim 14 in which the aromatic anhydride is an aromatic dianhydride.

16. Process according to claim 15 in which the aromatic dianhydride is polyfluorinated.

17. Process according to claim 15 in which the aromatic dianhydride is pyromellitic dianhydride.

* * * * *